United States Patent [19]
Ayers et al.

[11] Patent Number: 5,368,724
[45] Date of Patent: Nov. 29, 1994

[54] APPARATUS FOR TREATING A CONFINED LIQUID BY MEANS OF A PULSE ELECTRICAL DISCHARGE

[75] Inventors: Richard A. Ayers, El Cajon, Calif.; Richard H. Wesley, Houston, Tex.

[73] Assignee: Pulsed Power Technologies, Inc., Spring Valley, Calif.

[21] Appl. No.: 11,224

[22] Filed: Jan. 29, 1993

[51] Int. Cl.$^5$ ............................................. B01D 17/06
[52] U.S. Cl. ............................. 210/110; 210/243; 210/257.1; 204/306; 422/186.21; 422/186.28
[58] Field of Search ..................... 422/22, 23, 186.21, 422/186.23, 186.28; 210/109, 110, 138, 139, 143, 243, 257.1, 258, 744, 748, 198.1; 204/152, 164, 302, 306

[56] References Cited

U.S. PATENT DOCUMENTS

| | | | |
|---|---|---|---|
| 3,220,873 | 11/1965 | Wesley | 204/164 |
| 3,522,167 | 7/1970 | Allen | 422/22 |
| 3,594,115 | 7/1971 | Wesley et al. | 422/22 |
| 4,458,153 | 7/1984 | Wesley | 422/22 |
| 4,957,606 | 9/1990 | Juvan | 210/243 |
| 5,026,484 | 6/1991 | Juvan | 422/186.21 |

*Primary Examiner*—Joseph W. Drodge
*Attorney, Agent, or Firm*—Joseph H. Roediger

[57] ABSTRACT

Apparatus for purifying confined liquids and slurries by means of a spark discharge wherein the inner surface of the treatment vessel is designed to include a reflector section adjacent to a pair of electrodes and a concentrating section for intensifying the shock wave generated by the discharge between the electrodes. An external power source is coupled through a pulse forming network to the electrodes. The network is impedance matched to the impedance of the plasma arc generated between the electrodes to provide a high power pulse to the electrodes. The establishment of the plasma produces an extremely high pressure shock wave, u.v. radiation fringing on X-ray and electrohydraulic pressurization to alter the characteristics of the liquid therein.

18 Claims, 3 Drawing Sheets

APPARATUS FOR TREATING A CONFINED LIQUID BY MEANS OF A PULSE ELECTRICAL DISCHARGE

BACKGROUND OF THE INVENTION

This invention relates to apparatus for treating liquids and slurries by the use of a pulsed spark discharge between electrodes in a treatment vessel and, more particularly, to the purification of domestics, agricultural and industrial waters; sewage waste waters; industrial, chemical food processing and other toxic waste products; and the separation of dissolved sales and minerals, metals and other elements from liquids and slurries.

The increasing awareness of the need to treat liquid-like substances such as sewage, chemical and food-processing waste and other toxic waste products prior to their release into the surrounding environment has created a strong present interest in effective methods and apparatus for efficiently carrying out a purification process. One process described in U.S. Pat. No. 4,458,153 utilized the effects of a spark discharge produced between electrodes in combination with a localized magnetic field to alter the characteristics of confined liquid substances. Other investigations have resulted in limited volumes of liquid-waste being treated in a small confinement chamber, typically one liter or less, in which a spark discharge is established for a brief period. In this apparatus, a pair of electrodes are provided in the chamber with the pulsed energy from an external power source applied therebetween. The investigations have demonstrated that increased radiated power, shock waves and pressures in the vessel can be used to destroy micro-organisms in the liquid and effect purification thereof.

Results from spark discharge studies have been obtained using laboratory-size vessels to provide batch purification processing of small quantities of liquid waste. Primarily because of the energy requirements, the limited capacity of the treatment vessel and the use of batch treatment techniques, the spark discharge treatment method has not been commercially developed. Due consideration has not been given to the overall design of the confinement chamber so as to render it capable of use on a continuing basis for relatively large quantities of liquid waste. Furthermore, the energy consumption of known systems using a small confinement vessel is relatively large per unit of treated material. This characteristic is due in part to the lack of efficiency in the transfer of energy from the power source to the region between the exposed ends of the electrodes within the chamber.

In the confining vessel, the region between the electrode ends is the location of the spark discharge which generates the initial plasma channel. The transfer of energy to establish and expand the plasma channel is an important factor in generating the ultraviolet radiation, shock waves, electrohydraulic pressure and cavitation in the treatment vessel which produce the purification of the liquid waste. The amount of energy transferred to the plasma channel determines the amount of liquid waste that can be effectively treated in a single spark discharge for a particular designed chamber. Prior devices have been limited due to inefficient energy transfer and inadequate chamber design to the batch treatment of small quantities of liquid waste.

Accordingly, the present invention is directed to apparatus for treating liquid waste on a continuing basis wherein the efficiency of the energy transfer between power source and electrodes is improved. In addition, the treatment vessel of the apparatus is constructed to promote the effects produced by the spark discharge throughout the volume of liquid in the vessel. The combination of the features of the novel treatment vessel along with improvements in energy transfer permits treatment vessels of relatively large volume to be employed in the spark discharge treatment of liquid waste. Also, the present invention provides apparatus for continuing treatment of liquid waste without requiring lengthy interruptions in the movement of liquid waste material from a larger reservoir.

SUMMARY OF THE INVENTION

This invention is concerned with apparatus for treating liquid-like waste products by the use of a spark discharge occurring within a treatment vessel. The vessel is configured so that the liquid receives the benefits of the multiple effects of the spark discharge throughout a relatively large volume treatment vessel.

The apparatus includes a treatment vessel provided with input and output ports. Sealing means are located at the input and output ports and operate based on pressure differentials to permit a repetitive sequence of steps in the continuous operation of the apparatus. The treatment vessel has an inner surface which bounds the liquid treatment region and communicates with the input and output ports. The inner surface of the vessel includes a reflector section and a concentrator section. The reflector section is configured to distribute the produced effects to the concentrator section which promotes the treatment of the contents of the vessel.

Electrodes extend into the vessel with the tips thereof spaced adjacent the reflection section. All external pulse forming circuit is coupled to the electrodes for providing a series of voltage pulses between the electrodes. The spark discharge repetitively occurs between the electrodes in response to the application of voltage pulses therebetween. The discharge establishes a plasma in the liquid between the electrodes thereby creating a number of different effects throughout the treatment vessel. The effects include a plasma generated shock wave, short wavelength ultraviolet radiation and an electrohydraulic pressurization of the treatment vessel. These three produced effects combine to alter the characteristics of the liquid material within the treatment vessel to provide a purified liquid product.

The treatment vessel is provided with input and output ports with each port containing a sealing means for controlling the passage of liquid therethrough. The input port is normally coupled to a large volume reservoir which stores the untreated material. When the operation of the apparatus is initiated, material from the reservoir is urged under pressure into the treatment vessel through the input port. Control means is provided for regulating the supply of fluid to the input port and also for establishing the timing of the voltage pulses supplied to the electrodes. When the spark discharge occurs within the treatment vessel, the generation of the plasma between the electrodes produces multiple effects including a rapid increase in electrohydraulic pressure. The sealing means at the input and output ports are pressure responsive so that they seal the input and output ports during the time of treatment. When the increased pressure dissipates following treatment, the control means urges a new supply of untreated liquid into the treatment vessel through the input port and the treated material departs through the output port. The control means initiates the sequence of steps used in the repetitive process so that continual treatment of materials from the supply reservoir occurs.

The electrical conductivity of the plasma is a known constant established by ionization of the liquid adjacent the electrode tips. The average diameter of the plasma when first established can be measured so that for a particular electrode spacing, the average plasma impedance fails within a calculable range. The pulse forming network is provided with an impedance which is within the range of the impedance of the plasma channel so that energy is efficiently pumped into the plasma channel between the electrodes during the spark discharge. Thus, the matching of the impedances increases the peak power delivered to the plasma thereby enhancing the radiation from the plasma and the electrohydraulic pressuring of the liquid. The reflector section serves to direct the radiation and the shock wave produced into the concentrating section which distributes these treatment effects throughout the confinement chamber. As a result, it is possible to treat the liquid confined in a larger treatment vessel than heretofore possible and to affect this treatment with an increased energy efficiency.

Further features and advantages of the invention will become more readily apparent from the following detailed description of preferred embodiments thereof when taken in conjunction with the accompanying drawings.

DESCRIPTION OF THE PREFERRED EMBODIMENT

Figure 1:
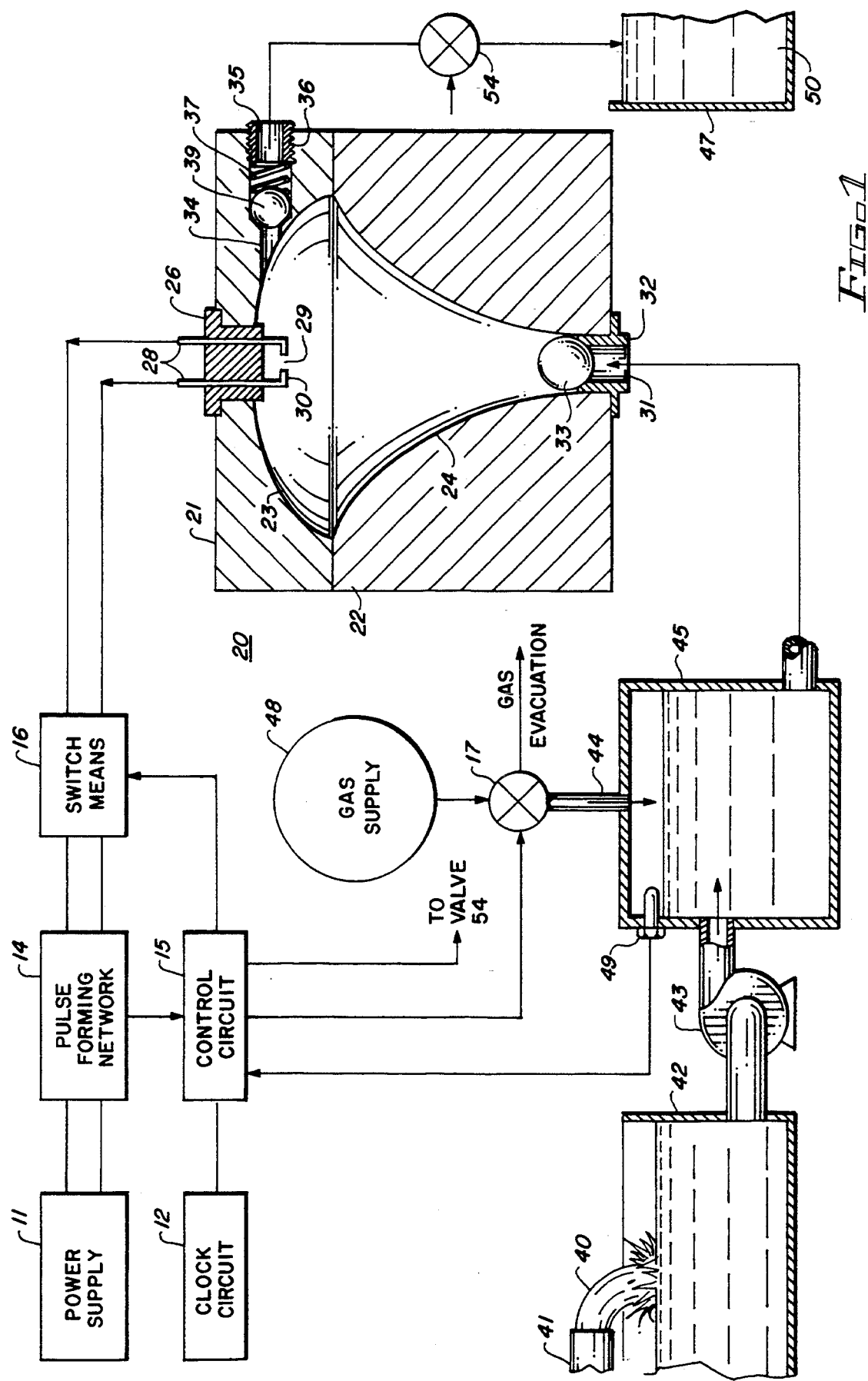
FIG. 1 is a block schematic diagram showing the liquid flow path in partial section of a preferred embodiment of the invention.

Referring now to FIG. 1, the apparatus includes a high strength treatment vessel 20 of approximately four liter capacity defining the volumetric region for receiving the liquid-like substance to be treated. The capacity of the vessel may be varied in accordance with the particular application without departing from the operating characteristics described herein. The term high strength is used herein to mean a high tensile, non-fatiguing metal alloy. The treatment vessel includes a reflector section 21 having a curved parabolic inner surface 23 which bounds and defines the upper portion of the liquid treatment region. While the preferred embodiment utilizes a parabolic curved surface 23 as a reflector, it is to be noted that a hemispherical inner surface may be utilized in other embodiments. Also, a mating concentrating section 22 is sealingly affixed thereto to form a unitary vessel and complete the volumetric treatment region. The inner surface 24 of the concentrator section which bounds the lower portion of the liquid treatment region is shown inwardly tapered. The volume available for liquid containment decreases in the concentrator with increasing distance from the reflector section. The concentrator section terminates at input port 31. An output port 35 laterally spaced from the electrode tips 30 is provided in the reflector section 21. In the embodiment shown, the tips were constructed of a metallic carbide for the high melting point and high impact resistance.

The treatment vessel 20 includes a central opening which receives an insulator plug 26 through which extend a pair of spaced electrodes 28, formed from a high temperature steel alloy. Each electrode 28 terminates in an electrode tip 30 separated by a spacing distance 29. As will later be explained, the spark discharge takes place across the spacing 29 between the ends of electrode tips 30. The external portions of the electrodes 28 are electrically coupled through switch means 16 to pulse forming network 14. The pulse forming network is coupled to the external power supply 11. A clock circuit 12 is provided to synchronize the operation of the circuit and its output is coupled to control circuit 15 which operates switch means 16 and gas valve 17.

The liquid-like substance 40 to be treated is shown in FIG. 1 as flowing from conduit 41 into reservoir 42. The substance is drawn from the reservoir 42 by pump means 43 connected to the bottom region of the reservoir and is transferred into a gas pressurizing chamber 45. While not necessary for all applications of the apparatus, the embodiment shown permits the liquid-like material contained in chamber 45 to have its dissolved gas content either increased or decreased by mechanical pumping means (not shown) coupled to valve 17. A gas supply 48 is connected to valve 17 so that compressed air or other gas contained therein at a higher pressure than the material in chamber 45 can be introduced into the chamber through the valve. A level sensor 49 is contained in the wall of chamber 45 with its output supplied back to a control circuit 15. If the level of liquid-like material in chamber 45 rises above the level sensor position 49, the valve 17 can be actuated to supply additional gas under pressure from supply 48 so that a nearly constant level of material can be maintained in chamber 45. Since the gas-liquid interface in chamber 45 is at a higher than ambient atmospheric pressure, additional gas is caused to be dissolved in the substance. When the material is transferred to the treatment vessel, the additional gas dissolved therein can be used to enhance one or more of the generated effects from the plasma discharge occurring in the treatment vessel. The liquid-like material is transferred under pressure from the chamber 45 through conduit 46 to input port 31 located at the base of the treatment vessel 20.

In the embodiment shown in FIG. 1, the treatment vessel generally comprises a lower concentrator section 22 having the input port 31 located therein and an upper reflector section 21 containing the output port 35. The input port 31 includes a valving mechanism shown as comprising seat 32 and ball 33. In the absence of internally generated pressure within the treatment vessel through the spark discharge between electrodes, the increased pressure of the liquid-like material in chamber 45 causes the ball 33 to be dislodged from seat 32 and the material of chamber 45 flows into and fills the treatment vessel 20. The output port 35 contains a normally biased open valve so that material in the chamber which has been previously subjected to the effects of a spark discharge is urged outwardly through the output port 35 into a retaining vessel 47. An output flow control valve 54 is shown located in the fluid line between output port 35 and vessel 47 to permit regulation of the output flow rate throughout a wide range of pressures established in chamber 45. As mentioned previously, valve 17 is used to vastly the pressure in the pressurizing chamber 45 in accordance with a signal from control circuit 15. In the embodiment shown, the control circuit provides a corresponding signal to valve 54 to regulate the flow rate from the treatment vessel.

The treated output flow from the vessel is shown as liquid 50 in vessel 47. The output port 35 contains a threaded valve seat 36, spring 37 and ball 39. A communicating channel 34 extends into the treatment volume of the vessel. When the liquid-like material is contained within the treatment vessel, the effects of the spark discharge between the electrodes includes an increase in pressure which drives the ball 33 down against seat 32 of the input port and also overcomes the bias of spring 37 to cause ball 39 to rest against seat 36 of the output port. Thus, the internal pressure during treatment is used to momentarily interrupt the regulated flow of fluid through the treatment vessel 20. While the particular valves shown are a gravity-fed valve at the input port of this concentrator section and a biased check valve at the output port, it is recognized that other types responsive to internally generated pressure can be employed if desired.

The treatment vessel 20 of FIG. 1 is machined in two parts, the reflector and concentrator sections, from a metal slug or rod. In the preferred embodiment, the reflector section 21 contains an inner surface which is paraboloid and of a diameter that is equal to the diameter of the adjacent portion of the treatment volume of the concentrator section 22. The insulator 26 with the electrodes 28 extending therethrough is centrally located in the reflector section with electrode tips 30 located at the focus of the parabolic curve. The concentrator section contains an inwardly tapered surface that extends 360° around the inner portion of the concentrator. The inner surface 24 which bounds the lower portion of the treatment volume is a surface of revolution about a vertical axis which provides a decrease in the cross-sectional area of the treatment volume with increasing distance from the electrode tips 30. The establishment of a spark discharge between the electrode tips 30 creates multiple effects through the creation of a plasma in a channel therebetween. It is important that these effects be transmitted throughout the bounded treatment volume and that all of the liquid-like material contained therein be subjected to the intense shock waves and pressure produced by the plasma as well as the radiation generated thereby. The failure to expose the entire volume of liquid to the full effects produced by the plasma may result in all output liquid 50 of generally unpredictable quality being passed from the treatment vessel.

The spark discharge generates a plasma in the channel between electrode tips. The plasma expands and launches a high velocity shock wave into the liquid-like substance contained within vessel 20. Also, at the same time the channel of plasma is established between the electrodes, an intense burst of high energy radiation is transmitted from the plasma channel throughout the entire treatment volume. This effect occurs due to the fact that the radiation generated is characterized by wavelengths short enough to penetrate both the liquid and the small particles contained in the liquid-like substances. Since the apparatus is effective with opaque liquid, the frequency of a substantial part of radiation transmitted is well-above the low energy portion of the ultraviolet spectrum. In the present case, these wavelengths approach the size of the wavelengths of radiation at the edge of the X-ray portion of the spectrum as a consequence of the plasma channel reaching a temperature of approximately 100,000 degrees K several microseconds after initiation of the spark discharge. As the plasma channel expands. The liquid-like material is further compressed and the electrohydraulic pressure increases substantially. In many cases, the pressure reaches 1,000 atmospheres in about 500 microseconds. The time required and pressure reached upon maximum expansion of the plasma channel is dependent on the amount of energy discharged into the plasma channel and the volume and configuration of the treatment region in the vessel. The self-actuating valves at the input and output ports immediately close in response to this electrohydraulic pressuring of the material to limit the pressure effects to only that liquid which is contained at that time within the treatment vessel. While this preferred embodiment uses check valves, other embodiment may be operated using either mechanical or electrical means synchronized to the flow rate through the treatment vessel to seal the input and output ports.

The spark discharge is generated from the output of a pulse generator which includes switch means 16, pulse forming network 14 and power supply 11. The pulse generator provides a high voltage, high current pulse of short duration to the pair of electrodes 28 thereby causing a breakdown in the liquid-like material residing in the volume between the electrode tips 30. The spark discharge occurs from one electrode tip to the other with a resultant plasma being formed in the volume therebetween. The plasma channel so formed generates multiple effects which are transmitted throughout the volume to alter the characteristics of the liquid-like material contained in the treatment vessel. The power supply 11 may include a step up transformer with a high voltage, three phase bridge rectifier to supply a charging current to the pulse forming network 14. Alternatively, a solid-state, high frequency inverter which can maintain unity power factor during the supplying of current to the pulse forming network can be employed. A variety of conventional transformer-rectifier charging means for network 14 are well known in the art.

The pulse forming network is charged to a preset voltage level by the charging current from the power supply and stores sufficient energy so that when the switch means 16 is closed, a pulse of electrical energy is provided to the electrodes 28 thereby causing the spark discharge therebetween. As shown in FIG. 1, control circuit 15 is provided to monitor the voltage level in the pulse forming network 14 and actuate switch means 16 only when the desired voltage level has been achieved. In addition, the control circuit receives the output signal from the fluid level sensing circuit and provides a corrective signal to valve 17 should there need to be a correction in the fluid level within the chamber 45. The clock signal from circuit 12 determines the rate of sampling of the voltage in the pulse forming network and can be used 10 synchronize sampling of other sensors utilized in this system as needed. The establishment of data sample rates for additional sensors if employed can be accomplished by conventional techniques.

Figure 2:
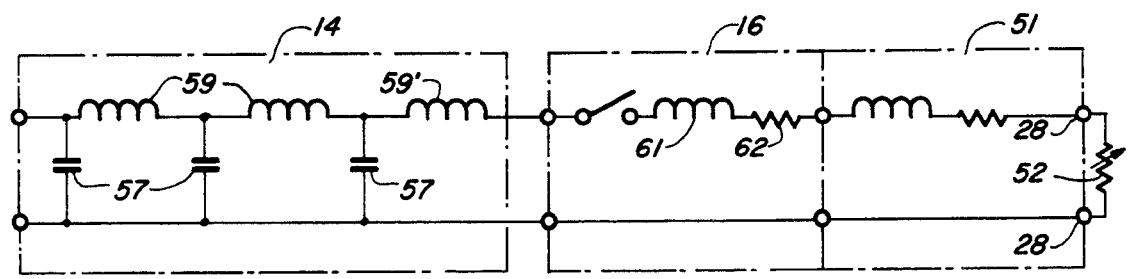
FIG. 2 is an electrical schematic diagram of the pulse forming network of the embodiment of FIG. 1.

The pulse forming network 14 is shown in further detail in the electrical schematic diagram of FIG. 2 along with switch means 16, the electrodes 28 and the power rail connection 51 thereto. The spark discharge and the plasma arc created thereby is shown as variable resistor 52 between electrodes 28. The pulse forming network 14 includes a number of capacitors 57 and inductors 59 with the inductors being coupled in series with the electrodes 28 and the capacitors 57 being coupled in parallel. The unidirectional current from the power supply 11 charges the capacitors 57 until the switch means 16 is actuated by a signal from the control circuit 15. At this moment, the energy stored in the capacitors is transferred to the electrodes through the switch means 16 and its internal inductance and resistance 61 and 62 respectively and the low inductance power rail connection 51 with its internal impedance. As a result, a spark discharge is developed between the electrode tips 30 creating a plasma channel in the liquid material between the electrodes. The transfer of energy occurs in the form of a pulse shown as the power pulse in FIG. 3. In the embodiment shown, the peak power level provided to the electrode circuit is in excess of one gigawatt during a period of 5 to 10 microseconds. The energy transfer must occur during this relatively short interval because the plasma channel expands and increases in volume and the high energy densities necessary to produce the effects relied upon for treatment of the liquid are difficult to obtain over longer periods.

The internal inductance 61 and resistance 62 of the switch means are minimized to reduce losses of power delivered to the electrodes. Similar care should be taken to minimize the inductive and resistive losses in the power rail connection 51. Maximum pulse power is attained in the plasma channel between the electrodes when the impedance of the pulse forming network is substantially matched to the average resistance 52 presented to the network 14 by the plasma established between the tips 30 of electrodes 28 during the power pulse period. The impedance during an interval of two to five microseconds after actuation of the switch 16 is used to determine the desired match. In the embodiment shown, the switch means 16 is preferably a triggered mercury-pool gas tube. The inductance 61 and resistance 62 associated therewith provide less than five percent of the corresponding value of inductance and resistance for the equivalent electrical circuit seen looking back from the electrodes 28. The contribution of the resistive effect of the power rail connection is minimal. In the case of the inductance associated therewith, its value may include a significant portion of the output inductance 59' of pulse forming network 14. Thus, the inductance 59' can be reduced in value by the computed amount of the inductance of the power interconnect if a substantial line length is necessary to provide power to the apparatus.

The characteristic impedance of the pulse forming network is a function of the square root of the network inductance divided by the network capacitance. The impedance of the plasma generated between the electrodes 28 is shown as variable resistor 52 and is a function of the electrode spacing which is 2.5 centimeters in the preferred embodiment, along with the diameter of the plasma channel established and the resistivity constant of a plasma. The constant is typically of the order of 12 milliohms per centimeter. The diameter of the plasma channel established increases as a function of the square root of the time taken from the initiation of the plasma. During the early formation of the plasma, in the first microsecond, its resistance decreases from several ohms into the 25 to 75 milliohm range which is the impedance range to be used in designing the pulse forming network. In operation, the pulse forming network acts as a higher impedance network during the initiation of the plasma. In order to provide the energy of between 10 to 100 kilojoules for the successful operation of the embodiment of FIG. 1, a power pulse width of approximately 10 microseconds is required. The equation for the pulse width of the discharge from the pulse forming network determines the acceptable values for the inductors 59 and the capacitors 57. The equation is $T=2(L \times C)^{0.5}$. The value of capacitance in the embodiment shown calculates to be about 135 microfarads. Thus, each paralleled capacitor 57 would have a value of one third that quantity. The inductance 59 is approximately 150 nanohenries so that each series inductor 59, 59' would be 50 nanohenries. This provides a characteristic impedance of the pulse forming network of about 34 milliohms. A pulse forming network 14 of the type shown in FIG. 1 when providing a 10,000 volt pulse stores in excess of 25 kilojoules.

Figure 3:
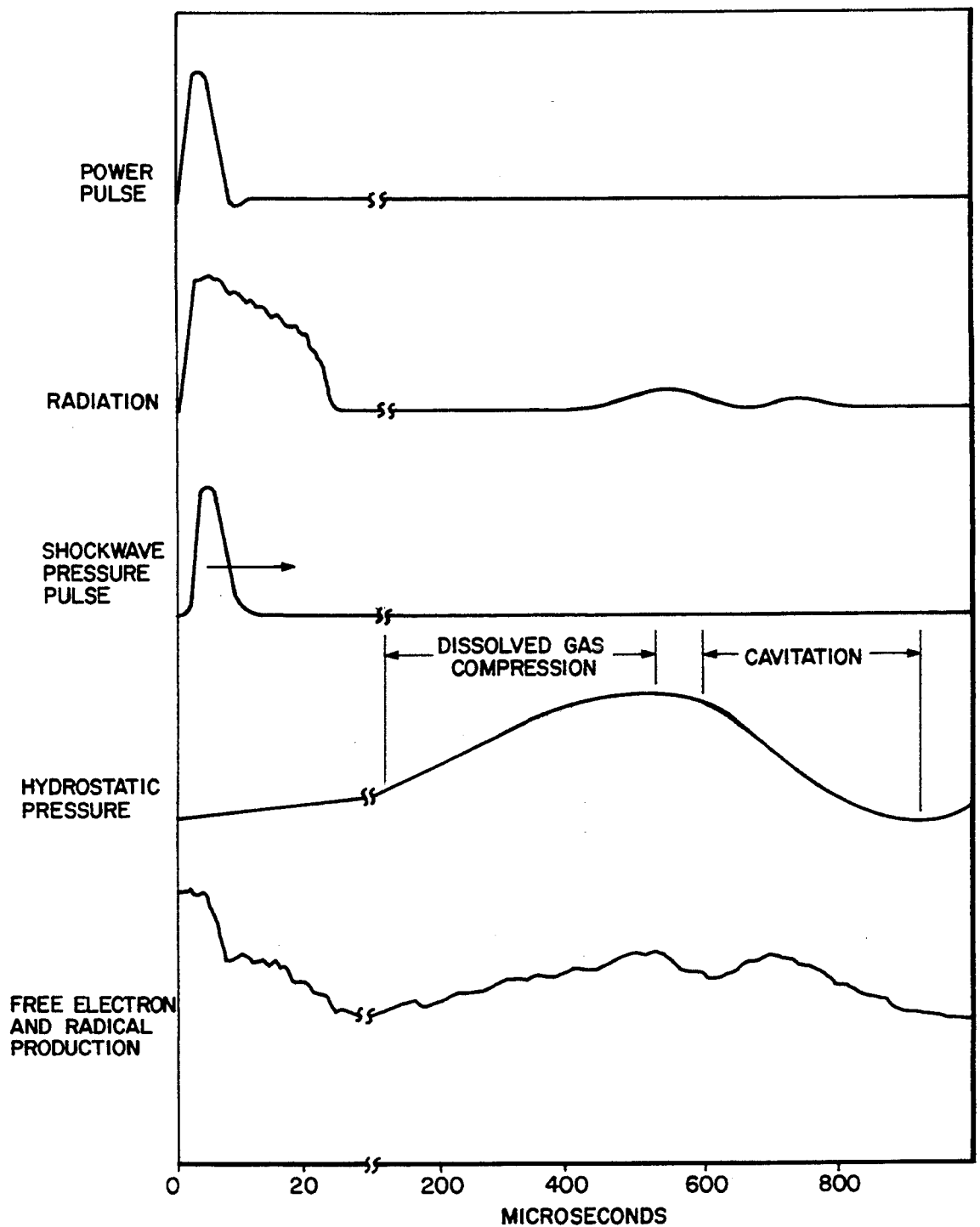
FIG. 3 is a series of wave forms showing the multiple effects generated within the treatment vessel of the embodiment of FIG. 1.

In operation, the establishment of the plasma in the treatment vessel exposes the material contained therein to multiple effects as shown by the wave forms of FIG. 3. The waveforms are plotted in two distinct time domains. The first domain is from the initiation of the spark discharge and the creation of the plasma up to 25 microseconds. The second time domain is from 200 to 1,000 microseconds. During the first time domain, the effects generated are occurring simultaneously with the initiation of the plasma channel, or lag it slightly. The immediate direct effect generated by the plasma is a high intensity burst of radiation lasting somewhat than the duration of the pulse from the pulse forming network 14. The radiation occurs as a burst due to the highly ionized state of the material forming the plasma. The wavelength of the radiation resides in the near X-ray region. Radiation of this wavelength has the capability to penetrate the entire volume of the treatment vessel to cause oxidation of the liquid-like material contained therein. For the embodiment of FIG. 1, the radiation is equivalent to a black body radiating temperature of over 100,000 degrees K.

A second direct effect produced by the expanding plasma channel is that of the launching of a shock wave having an initial pressure peak of nearly one million atmospheres as it breaks away from the expanding plasma channel during the first few microseconds. The channel initially is formed with a diameter of 1 to 3 mm and expands to about 5 cm. As this supersonic wavefront propagates outward from the plasma channel, it is reflected and deflected by the treatment region boundaries as it propagates therethrough in a few hundreds of microseconds. During this period of shock wave propagation, an extremely high compressive component resides in its leading edge region. A comparable tensile component develops in its trailing edge region. This tensile strain produces a cavitation effect in the liquid-like substance which is found to be useful in the generation of free radicals and electrons from the material. The compressive component of the shock wave results in a fracturing of any suspended solids. In operation of the embodiment of FIG. 1, solid particles within the range of 0.1 to 1 millimeter in diameter have been converted into nearly micron size. Another effect of the shock wave is in the tearing apart or breaking down of large molecules and microorganisms. Also, the shock wave changes the solubility product of dissolved solids by means of the extreme pressure gradient travelling through the treatment vessel. Material experiencing the shock wave is first compressed then quickly decompressed with the extreme pressure collapse causing a change in the solubility product thereby promoting precipitation of dissolved solids and facilitating recovery from the treated material.

A further effect of the high pressure pulse plasma established within the treatment vessel is the development of an electrohydraulic compression of the entire contents of the treatment vessel. As the plasma channel expands into a bubble with time, its volume increases thereby compressing the liquid within the vessel. The kinetic energy of the expanding plasma channel or bubble is expended in cooling from the induction of liquid into the plasma bubble during expansion until a pressure equalization is reached between the plasma bubble and the electrohydraulic pressure developed within the reaction vessel. A typical pressure balance of 1,000 atmospheres is reached in approximately 500 microseconds from the initiation of the plasma. Any dissolved gasses in the liquid-like material during this period are reduced in volume causing their temperature to increase to the point where ionization occurs thereby resulting in further free radical and electron production. When the plasma bubble ultimately collapses due to a massive loss of energy through its large surface area, the potential energy stored in the pressurized liquid causes the liquid to rush in to fill the volume formerly occupied by the plasma bubble. As the hydraulic pressure rapidly collapses, a tensile force is induced on the liquid in the wake of this collapse producing further cavitation with its associated free radical and electron generation. As can be seen in FIG. 3, the production of free electron and free radicals occurs at several intervals and for significant lengths of time during the one millisecond interval shown.

The significance of the extensive production of free radicals and electrons can be described as follows. Free electrons are absorbed by cations, especially metallic cations low on the electromotive force series, thereby reducing the cations to their elemental or nascent state. This process has applicability in both mineral extraction and toxic waste extraction operations. Free radicals such as the hydroxyl $(OH)^-$ produced in large populations throughout the treatment vessel act as a very powerful oxidizing agent to convert molecules such as hydrocarbons, fluorocarbons and the like to chemically inert components. Furthermore, the biochemical oxygen demand (BOD) of waste water and contaminated waters is significantly reduced by this advanced oxidation.

In operation, the embodiment of FIG. 1 has been successfully employed to treat a variety of different waste materials. Results obtained with the treatment of a slaughterhouse effluent showed that the biochemical oxygen demand (BOD) was reduced greater than 99%, the chemical oxygen demand (COD) was reduced greater than 95% and the reduction of fecal coliform bacteria was greater than 99.9%,. Tests performed on trailer park sewage showed a BOD reduction greater than 73%, a COD reduction of greater than 38% and a fecal coliform reduction greater than 99.9%. Similar operation using municipal sewage showed a BOD reduction of 82%, and a fecal coliform reduction greater than 99.95%. These results point out the ability of the present apparatus to render inactive contained microorganisms, oxidize bioactive content and reduce metallic cations in liquid materials. In addition, tests of the present apparatus have shown that metals can be extracted from solution and recovered by settling in the output reservoir.

Figure 4:
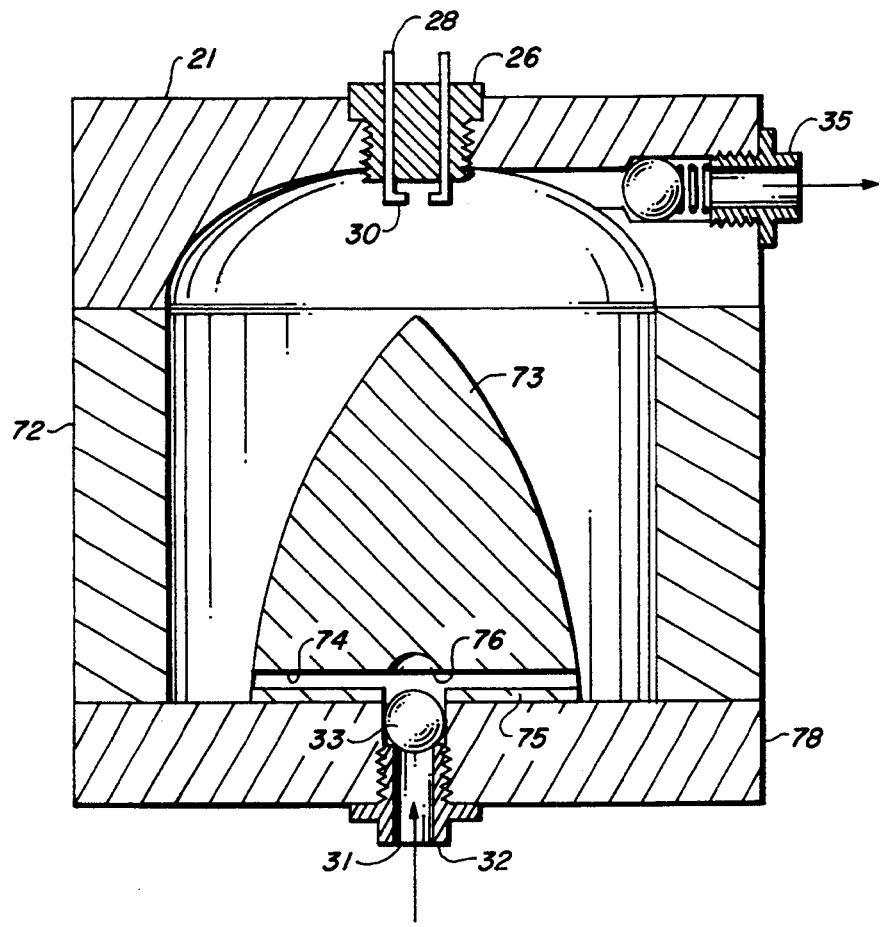
FIG. 4 is a cross-sectional view of a second embodiment of a treatment vessel suitable for use in connection with the embodiment of FIG. 1.

An additional embodiment of the treatment vessel used in the practice of the present invention is shown in FIG. 4. The reflector section 21 of the treatment vessel is similar in all respects to its counterpart shown in FIG. 1. The concentrator section 72 in FIG. 4 differs significantly from the embodiment of FIG. 1 in that it has a straight external wall section. As mentioned previously, the treatment vessel of FIG. 1 is machined from a metal slug or rod. However, the concentrator section of FIG. 4 is formed from large diameter straight walled tube stock which results in a substantial cost saving in construction. A separate shock wave deflection member 73 is centrally located in the treatment vessel to ensure that the shock wave generated by the establishment of the plasma propagates throughout the material contained in the vessel. The curvature of insert 73 accomplishes the same result as the curved or inwardly tapered walls of the concentrated section 22 in that the liquid treatment region decreases in cross-sectional area and unit volume with increasing distance from the electrode tips 30. The deflector is tapered in cross section as shown in FIG. 4. The bottom surface 75 of the deflector 73 is affixed to the base plate 78. Lateral communicating channels 74 are formed in the deflector above the bottom surface 75. The channels 74 communicate with and extend laterally from the input port 31 into the treatment region of the vessel. The valve seat 32 receives ball 33 to effect closure of the input port 31 when the pressure increases due to treatment of the contained material. A receiving depression 76 is formed in the adjacent portion of the insert to permit the ball 33 to clear the communicating channels 74 during the input of material into the vessel. The discussion of the effects produced by the high pressure pulse from the plasma established in the reflector section and transmitted downwardly throughout the concentrator section applies to both the embodiments of FIG. 1 and FIG. 4. The tendency for the effects to dissipate as the distance from the electrode tips increases is countered by the compensation provided by the inwardly tapered wall 24 of the embodiment of FIG. 1 and the generally conical shape of the deflector insert 73 of the embodiment of FIG. 4. The treatment of the liquid-like material contained in the vessels of both embodiments is the same and the wave forms of the effects shown in FIG. 3 apply to the effects occurring in both forms of treatment vessel.

While the above description has referred to particular embodiments of the invention, it is to be noted that many modifications and variations may be made therein without departing from the scope of the invention as claimed.

We claim:

1. Apparatus operable for treating a liquid by the use of a pulsed electrical discharge in a treatment vessel which comprises:
    a) a treatment vessel having an input port and an output port, said vessel having an inner surface defining a liquid treatment region including a reflector section and a concentrator section;
    b) sealing means located at said input and output ports for respectively controlling passage of liquid therethrough;
    c) electrode means contained within said vessel and spaced adjacent to the reflector section for establishing a plasma in said vessel, upon application of a voltage to said electrode means and creating a shock wave therein;

d) pulse forming means for supplying a series of electrical pulses to said electrode means; and e) control means for regulating supply of liquid to the input port and establishing the timing of pulses supplied to the electrode means, the resultant shock wave treating liquid present within the vessel.

2. The invention in accordance with claim 1 wherein said concentrator section defines a liquid treatment region which decreases in cross-sectional area with increasing distance from said electrode means.

3. The invention in accordance with claim 2 wherein said reflector section has a curved surface.

4. The invention in accordance with claim 3 wherein said electrode means is centrally located in the reflector section.

5. The invention in accordance with claim 4 wherein said control means comprises a normally open valve closed by differential pressure exerted by the liquid in the treatment vessel.

6. The invention in accordance with claim 2 wherein the concentrator section includes inwardly tapered walls with the input port located at the narrow base of the taper.

7. The invention in accordance with claim 2 further comprising a centrally-located tapered deflector spaced from the reflector section.

8. The invention in accordance with claim 7 wherein said deflector is affixed to said vessel adjacent the input port said deflector including transverse channels communicating with said input port.

9. The invention in accordance with claim 2 further comprising switch means coupled between said electrode means and the pulse forming means, said switch means being connected to the control means for actuation.

10. The invention in accordance with claim 9 wherein said pulse forming means comprises a plurality of series inductances and parallel capacitances having a characteristic impedance, said impedance being determined by the ratio of said inductances to said capacitances and made substantially equal to the impedance of the plasma channel when established within said vessel.

11. The invention in accordance with claim 2 further comprising an external reservoir communicating with the input port of the treatment vessel, and means for controlling the pressure of liquid in said reservoir.

12. The invention in accordance with claim 11 further comprising means for injecting gas into said reservoir to vary the gas content of the liquid therein.

13. The invention in accordance with claim 2 wherein said electrode means comprises a pair of electrodes extending into the treatment vessel from the reflector section terminating in spaced electrode tips.

14. The invention in accordance with claim 13 wherein said electrode tips are spaced approximately 2.5 centimeters apart.

15. The invention in accordance with claim 14 wherein said pulse forming means is impedance matched to the impedance of the plasma established between the electrodes in the treatment vessel.

16. The invention in accordance with claim 15 wherein said pulse forming means has a characteristic impedance within the range of 25 to 75 milliohms.

17. A vessel having a liquid treatment region for use with a plasma established therein, said vessel comprising:

a) a reflector section having a curved inner surface defining a portion of the liquid treatment region;

b) a concentrator section adjoined said reflector section to form a unitary vessel and having an inner wall surface extending from the curved inner surface of the reflector section and a base surface to bound the liquid treatment region;

c) a tapered deflector centrally located and projecting from the base surface of the concentrator section and spaced from the inner wall surface thereof, said deflector constructed and arranged for continuously decreasing the cross-sectional area of the liquid treatment region along the length of its projecting with increasing distance from the reflector section;

d) input and output ports located in said vessel and communicating with the liquid treatment region; and e) means for providing a pulsed electrical discharge in the liquid treatment region.

18. The invention in accordance with claim 17 wherein said deflector is affixed to said vessel adjacent the input port, said deflector including transverse channels communicating with said input port.

* * * * *